(12) United States Patent
Parthasaradhi Reddy et al.

(10) Patent No.: US 7,205,415 B2
(45) Date of Patent: Apr. 17, 2007

(54) PROCESS FOR THE PREPARATION OF SIMVASTATIN

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Kesireddy Subash Chander Reddy, Hyderabad (IN)

(73) Assignee: Hetero Drugs, Ltd., Hyderabad (IN)

( * ) Notice: Subject to any disclaimer, the term of this patent is extended or adjusted under 35 U.S.C. 154(b) by 0 days.

(21) Appl. No.: 10/539,736

(22) PCT Filed: Jan. 2, 2004

(86) PCT No.: PCT/IN2004/000003

§ 371 (c)(1),
(2), (4) Date: Jun. 20, 2005

(87) PCT Pub. No.: WO2005/066150

PCT Pub. Date: Jul. 21, 2005

(65) Prior Publication Data

US 2006/0094885 A1    May 4, 2006

(51) Int. Cl.
*C07D 309/30*       (2006.01)
(52) U.S. Cl. ...................................... 549/292
(58) Field of Classification Search ................. 549/292
See application file for complete search history.

(56) References Cited

U.S. PATENT DOCUMENTS 5,462,933 A * 10/1995 Kramer et al. .............. 514/176
5,763,646 A *  6/1998 Kumar et al. ................ 560/252
6,603,022 B1 *  8/2003 Sambasivam et al. ...... 549/292

* cited by examiner

*Primary Examiner*—D. Margaret Seaman
*Assistant Examiner*—Niloofar Rahmani
(74) *Attorney, Agent, or Firm*—Caesar, Rivise, Bernstein, Cohen & Pokotilow, Ltd.

(57) ABSTRACT

A process for manufacturing simvastatin is provided using novel intermediates. Thus, for example, lovastatin is reacted with methoxyethylamine, alpha methylated 2-methylbutyryl side chain of the amide formed, hydrolyzed and lactonized to produce finally simvastatin of high purity.

16 Claims, No Drawings

PROCESS FOR THE PREPARATION OF SIMVASTATIN

FIELD OF THE INVENTION

The present invention is related to a novel process for the preparation of simvastatin using novel intermediates.

BACKGROUND OF THE INVENTION

Simvastatin of formula I is known to be active inhibitors of HMG-CoA reductase. The therapeutic uses of simvastatin and related compounds were disclosed in U.S. Pat. No. 4,444,784.

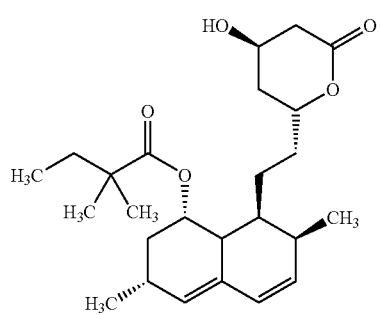

Various processes for preparing simvastatin were disclosed in the prior art. Processes described in the prior art for preparation of simvastatin can be summarized as under: 1) according to U.S. Pat. No. 4,444,784, lovastatin is hydrolyzed with lithium hydroxide to give lovastatin triol, lactonized to give a diol lactone, silylated 3-OH group, acylated and finally desilylated; 2) according to U.S. Pat. No. 4,582,915, lovastatin is hydrolyzed to give lovastatin potassium salt, directly C-methylated at alpha position of 2-methyl butyryl side chain and lactonized; 3) according to U.S. Pat. No. 4,820,850, lovastatin is reacted with monoalkylamine to produce lovastatin monoalkylamide, hydroxy groups are protected with t-butyidimethylsilyl groups, C-methylated at alpha position of 2-methyl butyryl side chain, deprotected, hydrolyzed the amide linkage and lactonized; 4) according to U.S. Pat. No. 5,763,646, lovastatin is reacted with monoalkylamine or monocycloalkylamine to produce lovastatin monoalkyl or cycloalkylamide, C-methylated at alpha position of 2-methyl butyryl side chain, hydrolyzed the amide linkage and lactonized; 5) according to U.S. Pat. No. 6,331,641 B1, lovastatin is hydrolyzed with a base to give lovastatin triol, lactonized to give a diol lactone, protected the hydroxy groups, acylated, deprotected and lactonized; 6) according to U.S. Pat. No. 6,603,022 B1, lovastatin is reacted with secondary amine to form a lovastatin amide, C-methylated at alpha position of 2-methyl butyryl side chain, hydrolyzed the amide linkage and lactonized; and 7) according to U.S. Pat. No. 5,393,893, hydroxyl groups of lovastatin alkylamide, cycloalkylamide or aralkyl amide are protected with phenyl boronic acid, C-methylated at alpha position of 2-methyl butyryl side chain, deprotected, hydrolyzed the amide linkage and lactonized.

The above processes suffer from one or other of the following defects. Selective silylation of triol intermediates is not satisfactory leading to the low overall yield and the contamination of the final product with unacylated impurity. Incomplete C-methylation of N-alkyl, cycloalkyl or aralkyl of lovastatinamide, which leads to contamination of simvastatin with lovastatin, thereby requiring additional purification steps.

The present invention provides a novel process for preparing simvastatin in high purity using novel intermediates. The novel process overcomes the aforesaid defects and is amicable for commercial scale production.

SUMMARY OF THE INVENTION

The present invention provides a novel process for preparing simvastatin using novel intermediates. The process for preparation of simvastatin of formula I:

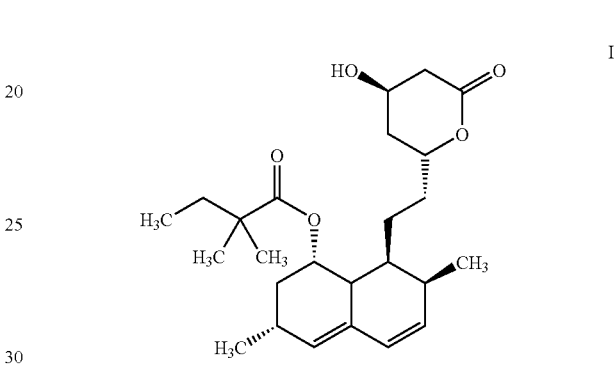

may be represented by the steps of:

a) reacting compound of formula II (lovastatin) or formula III:

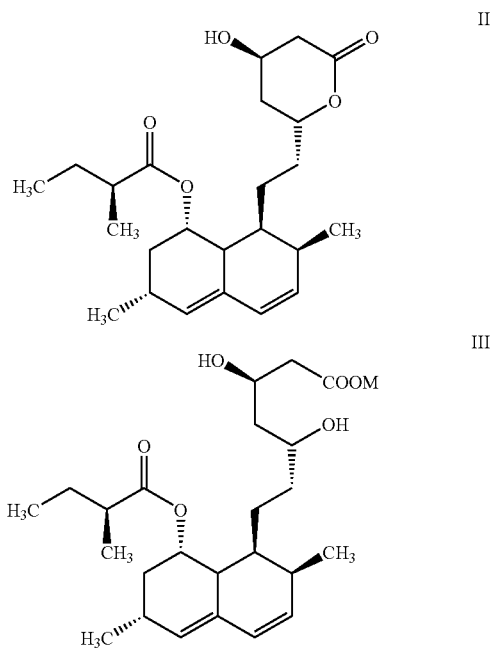

wherein M is H, metal ion or $NH_4$,
with the compound of formula IV:

$HNR_1R_2$            IV wherein
R₁ is —R₅—X—R₆ wherein
R₅ is alkyl, arylalkyl or cycloalkyl,
X is O or S and
R₆ is alkyl, arylalkyl, cycloalkyl or aryl; and
R₂ is independently selected from H, alkyl, cycloalkyl, arylalkyl and a group as defined for R₁;
or R₁ and R₂ may be bonded to form a cyclic ether or cyclic thio ether;
to produce a compound of formula V:

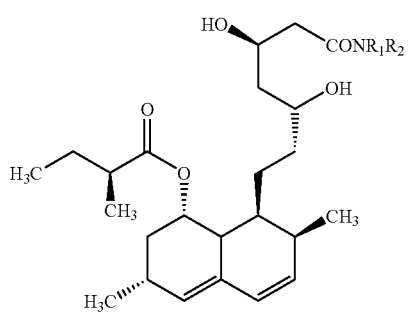

V wherein R₁ and R2 are as defined above,
(b) optionally protecting the two hydroxyl groups of the said compound of the formula V to produce a compound of the formula VI:

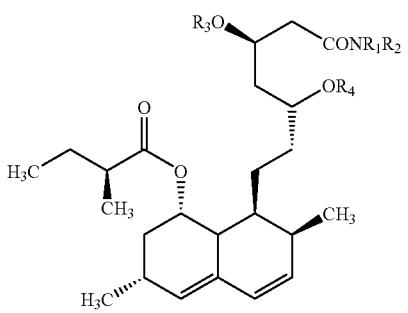

VI wherein R3 and R4 represents suitable protecting groups,
(c) methylating the said compound of formula V or VI to give a compound of formula VIIa or VIIb:

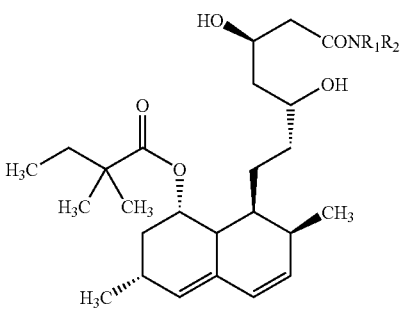

VIIa

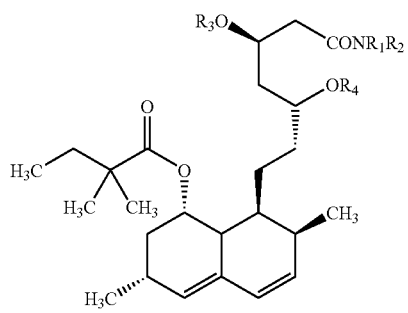

VIIb wherein R₁, R₂, R₃ and R₄ are as defined above, (d) hydrolyzing the amide group if the product of the above step is the said compound of formula VIIa or deprotecting the two protected hydroxy groups prior to hydrolysis if the product of the above step is the said compound of formula VIIb, optionally treating the hydrolyzed product with aqueous ammonia, to produce a compound of formula VIII:

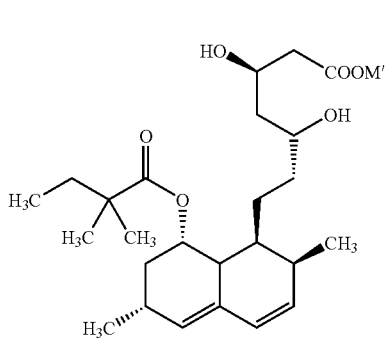

VIII wherein M' is a metal such as sodium or potassium or NH₄,
(e) lactonizing the said compound of formula VIII to produce simvastatin of formula I.

The intermediates of formula V, VI, VIIa and VIIb are novel.

DETAILED DESCRIPTION OF THE INVENTION

The present invention provides a novel process for preparing simvastatin using novel intermediates. The process for preparation of simvastatin of formula I:

may be represented by the steps of:
a) reacting compound of formula II (lovastatin) or formula III:

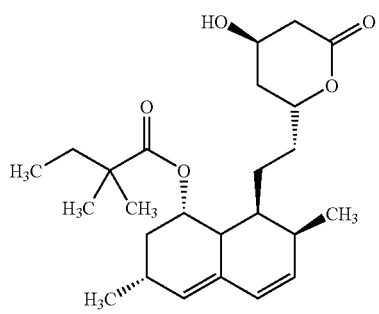

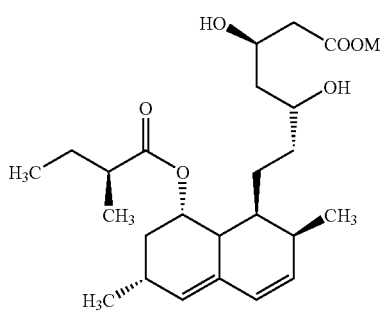

wherein M is H, metal ion or NH₄,
with the compound of formula IV:

$HNR_1R_2$       IV wherein
$R_1$ is —$R_5$—X—$R_6$ wherein
   $R_5$ is alkyl, arylalkyl or cycloalkyl,
   X is O or S and
   $R_6$ is alkyl, arylalkyl, cycloalkyl or aryl; and
$R_2$ is independently selected from H, alkyl, cycloalkyl, arylalkyl and a group as defined for $R_1$;
or R1 and R2 may be bonded to form a cyclic ether or cyclic thio ether;

to produce a compound of formula V:

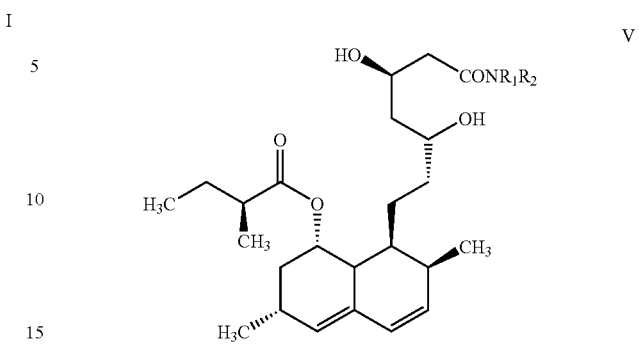

wherein $R_1$ and R2 are as defined above,
b) optionally protecting the two hydroxyl groups of the said compound of the formula V to produce a compound of the formula VI:

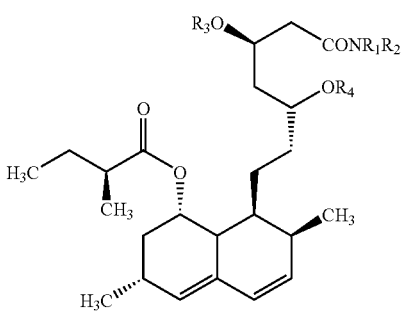

wherein R3 and R4 represents suitable protecting groups,
c) methylating the said compound of formula V or VI to give a compound of formula VIIa or VIIb:

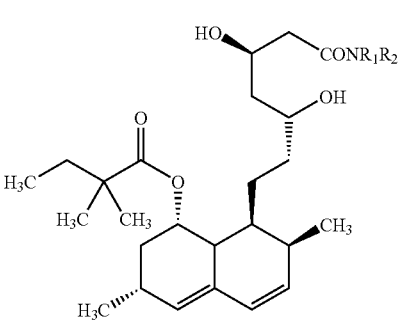

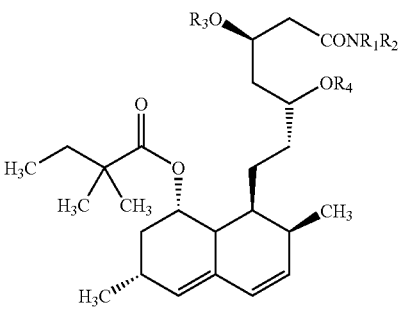

wherein $R_1$, $R_2$, $R_3$ and $R_4$ are as defined above, d) hydrolyzing the amide group if the product of the above step is the said compound of formula VIIa or deprotecting the two protected hydroxy groups prior to hydrolysis if the product of the above step is the said compound of formula VIIb, optionally treating the hydrolyzed product with aqueous ammonia, to produce a compound of formula VIII:

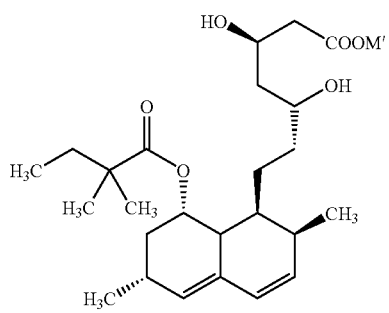

VIII wherein M' is a metal such as sodium or potassium or $NH_4$, e) lactonizing the said compound of formula VIII to produce simvastatin of formula I.

The suitable protecting groups are preferably selected from silyl protecting groups such as t-butyldimethylsilyl or trimethylsilyl groups.

Except otherwise stated the term alkyl refers to C1 to C10 straight or branched alkyl group, which is optionally substituted by such groups as alkoxy, thioalkoxy, aryloxy, arylthio.

The term aryl refers to phenyl, substituted phenyl, heteroaryl and substituted heteroaryl.

The term cycloalkyl refers to C3–C6-cycloalkyl.

The intermediates of formulae V, VI, VIIa and VIIb used in the process for preparing simvastatin are novel.

Lovastatin of formula II or a compound of formula III is reacted with an amine of formula IV to produce amide of formula V. The preferred groups of $R_1$ are methoxyethyl-, ethoxyethyl- and methoxymethyl-, more preferred being methoxyethyl and ethoxyethyl. The preferred groups of $R_2$ are H, methoxyethyl-, ethoxyethyl and methoxymethyl-, more preferred being H, methoxyethyl and ethoxyethyl. $R_1$ and $R_2$ together forming morpholinyl- with nitrogen of the formula IV is also preferable. The reaction is carried out in a solvent such as tetrahydrofuran.

The amide formed is C-methylated at alpha position of 2-methyl butyryl side chain of the said amide to produce a compound of formula VIIa. The amide of formula V is reacted with an alkali metal amide, wherein alkali metal is lithium, sodium or potassium, preferably lithium. The reaction is preferably carried out by combining a ethereal or hydrocarbon solution of the alkali metal amide to a ethereal solution of the compound of the formula V and stirring the contents for about 1–3 hours, the whole reaction being carried out at a temperature of below –30° C. under anhydrous conditions. To complete the C-methylation, methyl halide, preferably methyl chloride, methyl bromide or methyl iodide, most preferably methyl iodide, is added to the above reaction mass slowly for about 45 minutes to 2 hours and contents are stirred at a temperature of below –20° C. for about 10–60 minutes. The reaction mixture is quenched with an excess of water and washed with aqueous HCl. The organic layer is concentrated to give the methylated compound.

The alkali metal amide used in the above process is prepared by combining a hydrocarbon solution or ethereal solution of a n-butyl alkali metal with a dried solution of diethylamine dimethylamine, diisopropyl amine or pyrrolidine. Lithium pyrrolidide in tetrahydrofuran is the preferred the alkali metal amide solution.

The methylated compound formed as above is hydrolyzed with a metal hydroxide such as NaOH or KOH to produce a compound of formula VIII wherein M is metal, which is preferably isolated as the compound of formula VIII wherein M' is $NH_4$. The hydrolysis is preferably carried out in the medium containing an alcohol such as methanol and/or water and the contents are maintained usually at a temperature above 50° C. for about 2–10 hours, preferably 5–8 hours and then the solvent is distilled off under vacuum. Water is added and pH is adjusted to below 7 with an acid such as hydrochloric acid and the product is extracted into an organic solvent such as ethylacetate. The product is isolated as the ammonium salt by adding aq. ammonia solution.

The salt of formula VIII, preferably ammonium salt, formed above is suspended in a hydrocarbon solvent such as toluene and heated to about 90° C.–110° C. for 2–15 hours under a purge of nitrogen. The contents are cooled to 20° C.–30° C. and filtered and filtrate is concentrated under vacuum. A hydrocarbon solvent such as cyclohexane is added, refluxed for 10 to 60 minutes, then cooled to 5° C.–25° C., stirred for 1–12 hours, preferably for 2–5 hours. The lactone is filtered, washed with a hydrocarbon solvent such as cyclohexane and then dried under vacuum.

In an alternative method for the preparation of simvastatin of formula I, two hydroxy groups of the amide of formula V produced as described above is protected with a suitable protecting groups to produce a protected amide of formula VI, C-methylated at 2-methylbutyryl side chain of the said protected amide to produce a compound of formula VIIb, deprotected, hydrolyzed and lactonized to produce simvastatin of formula I.

Thus, the hydroxyl groups may be protected with silyl protecting groups such as t-butyldimethyl silylchloride, trimethylsilylchloride to obtain a compound of formula VI. C-methylation can be carried out essentially in the same manner as described above for unprotected amide for producing a compound of formula VIIb. Protecting groups are then removed by using, for example, HF or HCl and the unprotected compound thus formed is hydrolyzed and lactonized in the same manner as described as above for the compound of formula VIIa to produce simvastatin of formula I.

The invention will now be further described by the following examples, which are illustrative rather than limiting.

EXAMPLE 1

Step 1:

Lovastatin (50 gm) is mixed with tetrahydrofuran (100 ml) and methoxy ethylamine (140 ml) to obtain a clear solution, the solution is heated to 50° C. and stirred for 4 hours at the same temperature. Then the solvent is distilled off at reduced pressure not allowing the temperature to raise above 50° C., tetrahydrofuran (200 ml) is added to the residue thus obtained, stirred for 30 minutes and distilled off the solvent to give 58 gm of N-methoxyethyl-7-[1,2,6,7,8,8a(R)-hexahydro-2(S),6(R)-dimethyl-8(S)-[[2(S)-methylbutanoyl]oxy]-1(S)-naphthyl]-3(R),5(R)-dihydroxyheptanamide as residue (HPLC Purity 97.3%).

Step 2:

Tetrahydrofuran (520 ml) and pyrrolidine (90 ml) are mixed and the mixture is cooled to −40° C. n-Butyl lithium in hexane (1.6M, 510 ml) is added under nitrogen atmosphere for 2 hours at −40° C. to −50° C. The contents are stirred for 30 minutes at −35° C. to −40° C. The residue obtained in step 1 is dissolved in tetrahydrofuran (200 ml) and added to the alkali metal amide solution prepared above for 20 minutes at −40° C. to −45° C. The reaction mass is stirred for 1 hour at −40° C. to −45° C. The solution is warmed to −25° C. to −30° C., methyl iodide (29.7 ml) is added for 1 hour at −25° C. to −30° C. and stirred for 30 minutes at −25° C. to −30° C. Saturated ammonium chloride (55 ml) is added to the reaction mass for 10 minutes at −25° C. to −30° C., the solution is then allowed to raise the temperature to 25° C., water (250 ml) is added at 25° C. and stirred for 10 minutes. Then the layers are separated and the organic layer is washed with 100 ml of 2N hydrochloric acid. The organic layer is again washed with water (300 ml), dried on sodium sulfate and concentrated to 150 ml at reduced pressure not allowing the temperature to raise above 50° C. to give N-methoxyethyl-7-[1,2,6,7,8,8a(R)-hexahydro-2(S),6(R)-dimethyl-8(S)-[[2,2-dimethyl-butanoyl]oxy]-1(S)-naphthyl]-3(R),5(R)-dihydroxyheptanamide.

Step 3:

To the concentrate obtained in step 2 is added methanol (840 ml), water (550 ml) and sodium hydroxide (45 gm) at 25° C. The contents are heated to 75° C. and maintained for 7 hours at about 75° C. Then the solvent is distilled off at reduced pressure, cooled to 20° C. and water (400 ml) is added. Then the pH of the reaction mass is adjusted to 5 with 2N hydrochloric acid at 25° C., ethyl acetate (400 ml) is added and the pH is again adjusted to 3.5 with 2N hydrochloric acid solution. The layers are separated and the aqueous layer is washed with ethyl acetate (200 ml). The combined organic layer is dried on sodium sulfate. Ammonia solution, prepared by mixing aqueous ammonia (20 ml) and methanol (20 ml), is added to the reaction mass for 15 minutes at about 25° C., stirred for 1 hour at 25° C. and again for 1 hour at 0° C.–5° C. Then the separated solid is filtered and washed with chilled ethyl acetate (50 ml) to give 28 gm of simvastatin ammonium salt (HPLC Purity 97.5%).

Step 4:

The ammonium salt of step 3 (15 gm) is suspended in toluene (500 ml) and heated at 100° C. under a constant sweep of nitrogen for 5 hours. The solution is cooled to 25° C., activated charcoal (1 gm) is added stirred for 30 minutes and then filtered through celite-bed. The filtrate is concentrated under reduced pressure to a volume of 70 ml. Cyclohexane (200 ml) is added, refluxed for 20 minutes, cooled to 10° C. and stirred for 3 hours at 10° C. The precipitated solid is filtered and washed with cold cyclohexane (100 ml) and dried to obtain simvastatin as white crystalline product. The product is re-crystallized from absolute ethanol to obtain 13 gm of simvastatin (HPLC Purity 99.7%).

EXAMPLE 2

To N-Methoxyethyl-7-[1,2,6,7,8,8a(R)-hexahydro-2(S),6(R)-dimethyl-8(S)-[[2(S)-methylbutanoyl]oxy]-1(S)-naphthyl]-3(R),5(R)-dihydroxyheptanamide obtained by repeating the step 1 of example 1 is added dimethylformamide (175 ml) and the mixture is stirred for 1 hour. Imidazole (18 gm) and then tert-butyidimethylsilyl chloride (43 gm) are added. The mixture is stirred for 10 hours at 60° C. The contents are cooled to 10° C., methanol (10 ml) is added and stirred for 30 minutes at 10° C. Cyclohexane (500 ml) and water (575 ml) are added and product is extracted into cyclohexane layer. The layer is concentrated. The silyl protected lovastatinamide concentrate thus obtained is treated in the essentially same manner as described in step 2 to obtain N-methoxyethyl-7-[1,2,6,7,8,8a(R)-hexahydro-2(S),6(R)-dimethyl-8(S)-[[2,2-dimethyl-butanoyl]oxy]-1(S)-naphthyl]-3(R),5(R)-bis(t-butyldimethylsilyloxy)heptanamide. The methylated product obtained is dissolved in acetonitrile (250 ml), hydrofluoric acid (70 ml, 50% aqueous solution) is added. The mixture is stirred for 2 hours at 25° C., then cooled to 0° C. Aqueous sodium hydroxide (4N) is slowly added until the pH is raised to 7. The layers are separated, the organic layer is washed with water (250 ml) and concentrating at reduced pressure to obtain N-methoxyethyl-7-[1,2,6,7,8,8a(R)-hexahydro-2(S),6(R)-dimethyl-8(S)-[[2,2-dimethyl-butanoyl]oxy]-1(S)-naphthyl]-3(R),5(R)-dihydroxyheptan amide. The concentrate is treated in the essentially same manner as described in step 3 and then in step 4 to obtain simvastatin (HPLC Purity 99.6%).

We claim:

1. A process for the preparation of simvastatin of formula I:

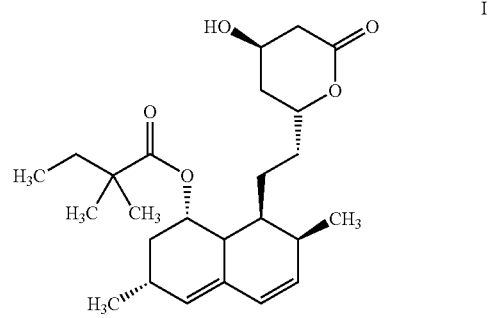

which comprises the steps of:

a) reacting compound of formula II (lovastatin):

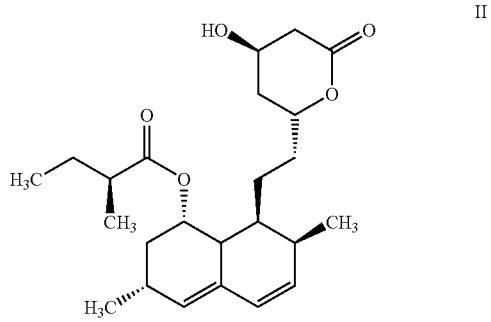

-continued

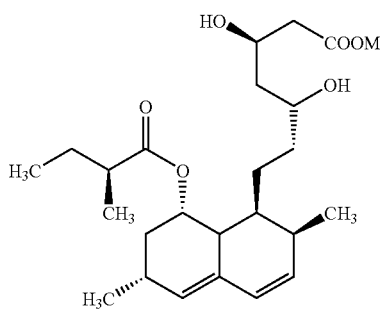

III with the compound of formula IV:

HNR₁R₂     IV wherein
$R_1$ is —$R_5$—X—$R_6$ wherein
$R_5$ is alkyl, arylalkyl or cycloalkyl,
X is O or S and
$R_6$ is alkyl, arylalkyl, cycloalkyl or aryl; and
$R_2$ is H;
to produce a compound of formula V:

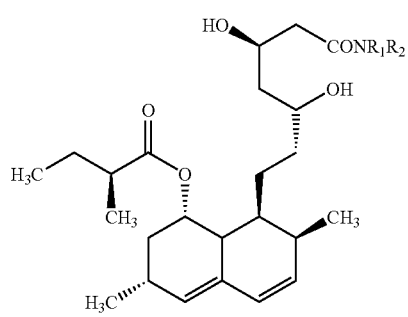

V wherein $R_1$ and $R2$ are as defined above, (b) optionally protecting the two hydroxyl groups of the compound of the formula V to produce a compound of the formula VI:

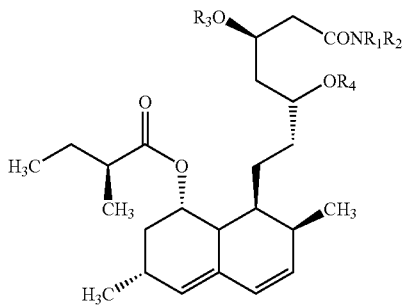

VI wherein R3 and R4 represents suitable protecting groups, (c) methylating said compound of formula V or VI to give a compound of formula VIIa or VIIb:

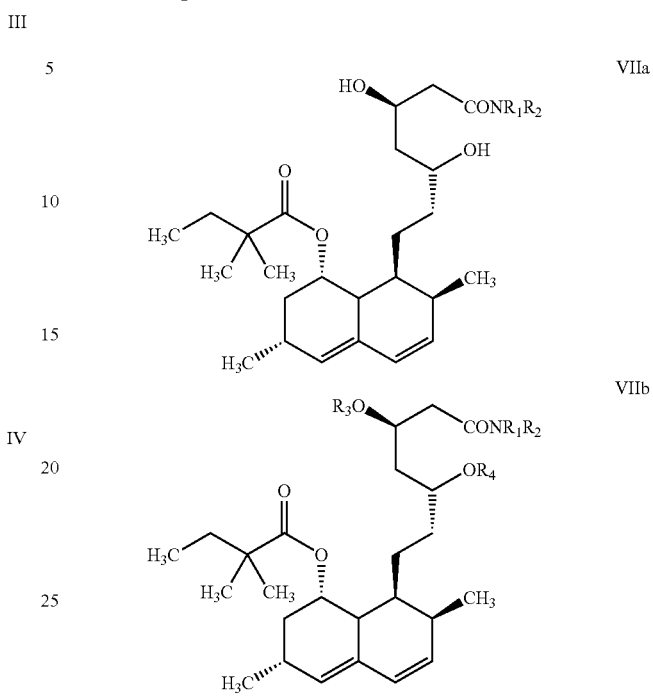

VIIa

VIIb wherein $R_1$, $R_2$, $R_3$ and $R_4$ are as defined above, (d) hydrolyzing the amide group if the product of the above step is said compound of formula VIIa or deprotecting the two protected hydroxy groups prior to hydrolysis if the product of the above step is said compound of formula VIIb, optionally treating the hydrolyzed product with aqueous ammonia, to produce a compound of formula VIII:

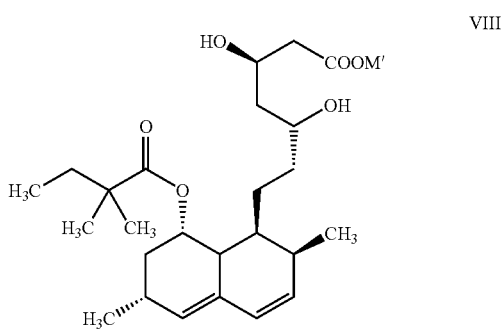

VIII wherein M' is a metal such as sodium or potassium or $NH_4$, and (e) lactonizing said compound of the formula VIII to produce simvastatin of formula I.

2. A process according to claim 1, wherein the hydroxy groups are not protected before methylation.

3. A process according to claim 1, wherein $R_1$ is selected from methoxyethyl, ethoxyethyl and methoxymethyl, and $R_2$ is H.

4. A process according to claim 2, wherein $R_1$ is selected from methoxyethyl, ethoxyethyl and methoxymethyl, and $R_2$ is H.

5. A process according to claim 1, wherein $R_1$ is methoxyethyl and $R_2$ is H.

6. A process according to claim 2, wherein $R_1$ is methoxyethyl and $R_2$ is H.

7. A process according to claim 3, wherein $R_1$ is methoxyethyl and $R_2$ is H.

8. A process according to claim 4, wherein $R_1$ is methoxyethyl and $R_2$ is H.

9. A process according to claim 1, wherein methylation is carried out using an alkali metal amide and a methyl halide.

10. A process according to claim 9, wherein the alkali metal is lithium, sodium or potassium; and the methyl halide is methyl iodide, methyl chloride or methyl bromide.

11. A process according to claim 9, wherein the alkali metal amide is lithium pyrrolidide and the methylhalide is methyl iodide.

12. A process according to claim 10, wherein the alkali metal amide is lithium pyrrolidide and the methylhalide is methyl iodide.

13. A process according to claim 1, wherein the starting compound is lovastatin of the formula II.

14. A process according to claim 1, wherein $R_3$ and $R_4$ represent silyl protecting groups.

15. A process according to claim 14, wherein the silyl protecting groups are selected from t-butyldimethylsilyl and trimethylsilyl groups.

16. A process according to claim 1, wherein:

i) lovastatin is treated with methoxyethyl amine in an organic solvent to produce the compound of the formula V wherein $R_1$ is methoxyethyl- and $R_2$ is H, ii) methylating the product obtained in the previous step with lithium pyrrolidide in tetrahydrofuran and methyl iodide to produce the compound of the formula VIIa wherein $R_1$ is methoxyethyl- and $R_2$ is H, iii) hydrolyzing the product obtained in the previous step with a strong base to obtain the compound of the formula VIII, iv) adding aqueous ammonia to the product obtained in the previous step to produce simvastatin ammonium salt, and v) lactonizing the product obtained in the previous step to produce simvastatin.

* * * * *